(12) United States Patent
Li et al.

(10) Patent No.: US 9,632,041 B2
(45) Date of Patent: Apr. 25, 2017

(54) COMPUTED TOMOGRAPHY DEVICE BASED ON STRAIGHT TRAJECTORY AND X-RAY IMAGING DEVICE

(71) Applicants: NUCTECH COMPANY LIMITED, Haidian District Beijing (CN); Tsinghua University, Haidian District Beijing (CN)

(72) Inventors: Mingliang Li, Haidian District Beijing (CN); Zhiqiang Chen, Haidian District Beijing (CN); Yuanjing Li, Haidian District Beijing (CN); Jianmin Li, Haidian District Beijing (CN); Li Zhang, Haidian District Beijing (CN)

(73) Assignees: NUCTECH COMPANY LIMITED, Haidian District, Beijing (CN); TSINGHUA UNIVERSITY, Haidian District, Beijing (CN)

( * ) Notice: Subject to any disclaimer, the term of this patent is extended or adjusted under 35 U.S.C. 154(b) by 275 days.

(21) Appl. No.: 14/494,301

(22) Filed: Sep. 23, 2014

(65) Prior Publication Data
US 2015/0085973 A1 Mar. 26, 2015

(30) Foreign Application Priority Data
Sep. 23, 2013 (CN) .......................... 2013 1 0436220

(51) Int. Cl.
*A61B 6/02* (2006.01)
*G01N 23/04* (2006.01)
(Continued)

(52) U.S. Cl.
CPC .......... *G01N 23/046* (2013.01); *A61B 6/035* (2013.01); *G01T 1/2985* (2013.01); *G21K 1/025* (2013.01);
(Continued)

(58) Field of Classification Search
CPC .......... A61B 6/03; A61B 6/032; A61B 6/035; A61B 6/06; A61B 6/4429; A61B 6/4452;
(Continued)

(56) References Cited

U.S. PATENT DOCUMENTS 3,790,799 A * 2/1974 Stein ...................... G01N 23/04
250/366
3,944,833 A * 3/1976 Hounsfield ............ A61B 6/032
250/367

(Continued)

FOREIGN PATENT DOCUMENTS

WO 2014/052665 A1 4/2014

*Primary Examiner* — Thomas R Artman
(74) *Attorney, Agent, or Firm* — Knobbe Martens Olson & Bear LLP (57) ABSTRACT

A straight trajectory CT device can be used in radiation imaging. The device includes: a ray-generating unit that generates a ray within a specific range of field angle; a channel for an object to be inspected though which the object to be inspected passes; a first collimator; and a ray receiving unit provided on both sides of the channel for the object to be inspected. The ray beam is received by the ray receiving unit after penetrating the first collimator and the object to be inspected in order. The ray generating unit is static and the first collimator moves in the same direction as the ray receiving unit. This direction is parallel to the channel for the object to be inspected. The device can complete computed tomography with a minimum of one ray receiving unit, thereby simplifying the structure of the device and reducing its cost.

12 Claims, 6 Drawing Sheets

(51) Int. Cl.
　　　*A61B 6/03*　　　(2006.01)
　　　*G21K 1/02*　　　(2006.01)
　　　*G01T 1/29*　　　(2006.01)
　　　*A61B 6/06*　　　(2006.01)

(52) U.S. Cl.
　　　CPC ............... *A61B 6/032* (2013.01); *A61B 6/06* (2013.01); *G01N 2223/3301* (2013.01)

(58) Field of Classification Search
　　　CPC ......... G01N 23/046; G01N 2223/3301; G01V 5/005; G01V 5/0066
　　　See application file for complete search history.

(56) References Cited

U.S. PATENT DOCUMENTS

| | | | | |
|---|---|---|---|---|
| 4,096,391 | A | * | 6/1978 | Barnes ................... G21K 1/025 378/146 |
| 4,099,060 | A | * | 7/1978 | Franke ..................... A61B 6/06 378/11 |
| 4,686,695 | A | * | 8/1987 | Macovski ............... A61B 6/032 348/E5.089 |
| 2015/0092910 | A1 | | 4/2015 | Xing |

* cited by examiner

COMPUTED TOMOGRAPHY DEVICE BASED ON STRAIGHT TRAJECTORY AND X-RAY IMAGING DEVICE

CROSS-REFERENCE TO RELATED APPLICATION

This application claims priority to Chinese Patent Application No. 201310436220.4 filed on Sep. 23, 2013, the disclosure of which including the specification, the drawings, and the claims is hereby incorporated by reference in its entirety.

TECHNICAL FIELD

The present disclosure relates to a computed tomography device, and more particularly, a computed tomography device based on straight trajectory and an X-ray imaging device, which belongs to the field of radiation imaging.

BACKGROUND

Because X-ray has excellent penetrability and regular attenuation character, a computed tomography (断层打描, CT for short) device based on X-ray have wide applications in security check, nondestructive detection, medical examination etc. A CT device mainly includes a ray generating unit, a ray receiving unit and an imaging computer and so on. When a CT device performs radiation imaging, the CT device scans around the object to be inspected through various angles. The ray generated by the ray generating unit irradiates the object to be inspected to produce projection data. The receiving unit receives the projection data and transmits the projection data to the imaging computer. The imaging computer identifies the received projection data, and reconstructs the projection data to obtain the tomography information of the object to be inspected, thereby the structure and composition of the object to be inspected may be demonstrated directly and clearly. Recently, the scanning trajectories of the CT device are arc, spiral, straight line and saddle and so on.

In current technology, the straight trajectory CT device has gained more and more attention and research because it employs straight trajectory scanning instead of conventional circular or spiral trajectory scanning and so on. The straight trajectory CT device in current technology uses the ray beam generated by the ray generating unit to perform straight trajectory scanning on the object to be inspected, a large number of ray receiving units are provided on the straight track to receive the ray beam, And the ray receiving unit includes detectors, radiation guard components etc. Thus, the cost of the straight trajectory CT device is increased dramatically because of use of a large number of detectors and radiation guard components, which limits the spread and the application of the straight trajectory CT device seriously.

Therefore, there is a problem to be solved quickly to provide a straight trajectory CT device at low cost.

SUMMARY

The technical problem of the present application is to provide a straight trajectory CT device with simple structure, which is easy to implement and of low cost.

In order to realize the invention aim, the present invention is provided with a computed tomography device based on straight trajectory and an X-ray imaging device.

On the one hand, the present invention is provided with a computed tomography device based on straight trajectory which includes a ray generating unit for generating ray beam within a specific range of field angle, a first collimator for restraining the ray beam; a channel for an object to be inspected though which the object to be inspected could pass; and a ray receiving unit for receiving the ray beam arranged in order;

the ray beam generated by the ray generating unit is received by the ray receiving unit after penetrating the first collimator and the object to be inspected in order, and the ray receiving unit transmits the received ray beam data to an imaging computer to process and display the data;

the ray generating unit is static and the first collimator moves toward the same direction as the ray receiving unit moves toward.

Wherein, preferably, at least one first collimating slit through which the ray beam passes is provided on the first collimator;

the first collimating slit is ranging within the range of field angle, and the boundary of first collimator is beyond the range of the field angle.

Wherein, preferably, the number of the first collimating slits is n; when n equals to 1, the maximum stroke of the unidirectional movement of the first collimating slit at a time is s; when n is larger than 1, the distance between the centers of adjacent first collimating slits equals to s/n.

Wherein, preferably, the number of the ray receiving units is equal to the number of the first collimating slits, and each ray receiving unit corresponds to one of the first collimating slit.

Wherein, preferably, the ray receiving unit comprises the third collimator provided with the third collimating silt and a detector receiving the ray beam that penetrates the third collimator.

Wherein, preferably, the ray generating unit comprises the ray source generating ray beam and the second collimator which defines the ray beam in the specific range of field angle.

Wherein, preferably, the device further comprises the first track and the second track parallel to each other provided on both sides of the moving channel, the first collimator moves on the first track, and the ray receiving unit moves on the second track; the ratio of the velocity of movement of the first collimator to the second collimator is equal to the ratio of the distance from the ray source to the first track and the distance from the ray source to the second track.

Wherein, preferably, the first track and the second track are straight track parallel to the moving channel; or the first track and the second track are arc tracks whose centers is the ray generating unit.

Wherein, preferably, the ray generating unit, the first collimator and the ray receiving unit are fixed on a straight bar.

Wherein, preferably, the ray receiving unit further comprises a radiation guard component for absorbing the ray beams which are not absorbed by the ray receiving unit.

Wherein, preferably, when perform tomography scanning, the object to be inspected moves in the moving channel, and the first collimator and the ray receiving unit perform reciprocation.

Wherein, preferably, the velocity of the object to be inspected is 0.5 percent to 10 percent of the velocity of the ray receiving unit.

Wherein, preferably, the device further comprises a control unit capable of controlling and monitoring the moving condition of the first collimator and the ray receiving unit.

On the other hand, the present application further provides a straight trajectory X-ray imaging device which includes:

a ray generating unit for generating ray beam within a specific range of field angle, a first collimator for restraining the ray beam; a channel for an object to be inspected though which the object to be inspected could pass; and a ray receiving unit for receiving the ray beam arranged in order;

the ray beam generated by the ray generating unit is received by the ray receiving unit after penetrating the first collimator and the object to be inspected in order, and the ray receiving unit transmits the received ray beam data to an imaging computer to process and display the data;

the ray generating unit is static and the first collimator moves toward the same direction as the ray receiving unit moves toward;

when performing scanning, the object to be inspected is static in the moving channel; the first collimator and the ray receiving unit perform a unidirectional movement for only once.

According to the CT device based on straight trajectory provided by the present application, by the first collimator provided between the ray receiving unit and the channel for the object to be inspected, the ray beam is received by the ray receiving unit after penetrating the first collimator and the object to be inspected in order. During scanning, the ray generating unit is static and the first collimator moves toward the same direction as the ray receiving unit moves toward and the moving direction is parallel to the channel for the object to be inspected. The scanning of the object to be inspected for each angle is achieved by the collaborating movement between the first collimator and the ray receiving unit. Therefore, the straight trajectory CT device of the present application can complete tomography scanning with the least one ray receiving unit, thereby simplifying the structure of the straight trajectory CT device and reducing its cost.

DETAILED DESCRIPTION OF THE PREFERRED EMBODIMENTS

Detailed description of the present invention is given in combination with the accompanying drawings and embodiments. The following embodiments are merely for the purpose of illustration and not intended to limit the scope of the present invention.

Figure 1:
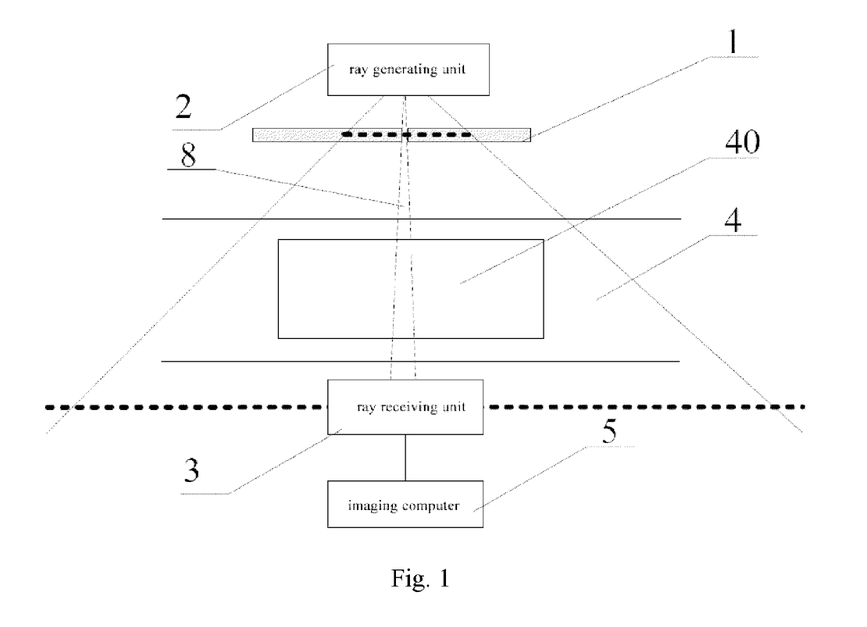
FIG. 1 is a schematic view of the structure of a straight trajectory CT device according to embodiment 1 of the present invention.

As shown in FIG. 1, the CT device based on straight trajectory of the present disclosure includes a ray generating unit 2 for generating ray beam 8 within a specific range of field angle, a first collimator 1 for restraining the ray beam 8; a channel 4 for an object 40 to be inspected though which the object to be inspected could pass; and a ray receiving unit 3 for receiving the ray beam 8 arranged in order; the ray beam 8 generated by the ray generating unit 2 is received by the ray receiving unit 3 after penetrating the first collimator 1 and the object 40 to be inspected in order, and the ray receiving unit transmits the received ray beam data to an imaging computer to process and display the data; the ray generating unit 2 is static and the first collimator 1 moves toward the same direction as the ray receiving unit 3 moves toward.

Detailed description of the present invention is given in combination with the accompanying embodiments.

Embodiment 1

As shown in FIG. 1, the straight trajectory CT device of the present disclosure includes a ray generating unit 2, a first collimator 1, a channel 4 for the object to be inspected, a ray receiving unit 3, and an imaging computer 5 etc arranged in order; the ray generating unit 2 is configured to generate a ray beam 8 within a range of a specific angle, e.g., a range of an angle of 90 degree, or a range of an angle of 120 degree etc. The first collimator 1 is configured to further define the ray beam 8, so that the ray beam 8 is formed to a very narrow range after passing the first collimator 1. The channel 4 for the object to be inspected is used for the object 40 to be inspected to pass through. The ray generating unit 2 and the first collimator 1 are provided on one side of the channel 4 for the objects to be inspected, and the ray receiving unit 3 is provided on the other side of the channel 4. After the ray beam penetrates the first collimator 1 and the object 40 to be inspected respectively, the ray beam is received by the ray receiving unit 3. The ray receiving unit 3 transmits the received ray beam data to the imaging computer 5; the imaging computer 5 reconstructs and displays the ray beam data. The main improvement of the present disclosure is that when the scanning is performed to the object 40 to be inspected, the ray generating unit 2 is kept static while the first collimator 1 and ray receiving unit 3 are moving straight toward the same direction which is parallel to the channel 4 for the object to be inspected. The scanning of the object 5 to be inspected in each angle is achieved by the collaborating movement between the first collimator 1 and the ray receiving unit 3. Therefore, the straight trajectory CT device of the present disclosure may complete tomography scanning with a minimum of one ray receiving unit 3, so as to simplify structure of the straight trajectory CT device and to reduce the cost of the straight trajectory CT device, as well as to provide technical support for the spread of straight trajectory CT in container, for example. Because the tomography image of the object 40 to be inspected may be obtained by the straight trajectory CT device according to the present disclosure, it may solve the problem of the overlapping of images in the conventional X-ray imaging.

The structure of the straight trajectory CT device of the present disclosure is simpler than the straight trajectory CT device of current technology. The weight of the straight trajectory CT device of the present disclosure is lighter and easier to carry than the straight trajectory CT of the current technology. Thus, the straight trajectory CT device of the present disclosure may be designed to be a portable device instead of being fixed at one place. Because the first collimator 1 in the straight trajectory CT device of the present disclosure may define the ray beam 8 in a range of a narrow angle, it may reduce the impact on the quality of the tomography imaging caused by the scattering. Meanwhile, because the straight trajectory CT device of the present disclosure only uses a small number of ray receiving units 3, the signal crosstalk between the ray receiving units 3 is reduced, and the precision of imaging is improved. Because a large number of ray receiving units 3 are saved, the system of the present disclosure is capable of employing the ray receiving units 3 of higher performance as necessary, e.g. the ray receiving units 3 of lower afterglow effect, sandwiched dual energy ray receiving units 3, or the ray receiving units 3 with higher energy resolution etc.

Embodiment 2

Figure 2:
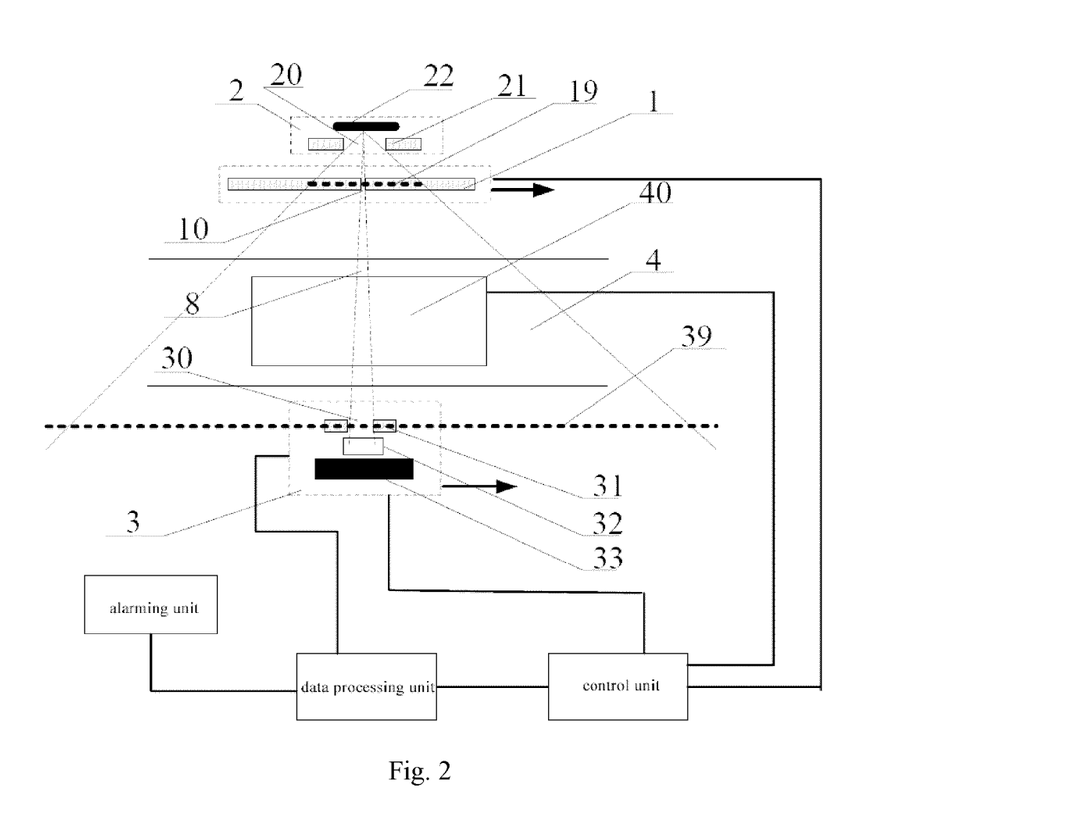
FIG. 2 is a schematic view of the structure of a straight trajectory CT device according to embodiment 2 of the present invention.

The straight trajectory CT device according to the current embodiment is shown in FIG. 2. The embodiment 2 is substantially similar to embodiment 1. The straight trajectory CT device comprises a ray generating unit 2, the first collimator 1, a channel 4 for the objects 4 to be inspected, a ray receiving unit 3 and an imaging computer 5 or the like arranged in order.

The distinction from embodiment 1 mainly lies in that the ray generating unit 2 may include a ray source 22 generating the ray beam 8 and a second collimator 21 defining the ray beam 8 within a range of a specific angle. The ray source 22 may be an X-ray machine, an electron accelerator ray source or an isotopic source etc. For example, for the X-ray machine or the electron accelerator ray source, a target material may be provided at the ray source 22. The electron beam of X-ray machine or the electron beam ejected by the electron accelerator is bombarded on the target material so as to generate the X-ray. A second collimating slit 20 is provided on the second collimator 21. On the one hand, the second collimator 21 is configured to allow a portion of the ray beam 8 generated by ray source 22 to penetrate the second collimating slit 20 for the purpose of collimation. On the other hand, the second collimator 21 is configured to absorb and obstruct the other portion of the ray beam 8 that does not penetrate the second collimating slit 20 for the purpose of radiation guard.

The first collimator is disposed on the ejecting direction of the ray beam 8 of the ray source 22; the first collimator 1 is provided with a first collimating slit 10 and is used to further define the ray beam 8. After the ray beam penetrates the first collimator 1, the ray beam 8 is formed to the range of narrow angle. The first collimating slit 10 is set within the range of the field angle while the boundary of the first collimator 1 is wider than the specific range of the field angle defined by the ray generating unit 2. That is, no matter where the first collimator 1 moves, the first collimator 1 should entirely cover the specific range of the angle defined by the ray generating unit 2 so as to absorb and obstruct the ray beam 8 that does not pass the first collimating slit 10 for the purpose of radiation guard.

In the embodiment, the ray receiving unit 3 includes a third collimator 31 with a third collimating slit 30 and a detector 32 receiving the ray beam 8 that has penetrated the third collimator 31. After the ray beam 8 penetrating the first collimating slit 10 penetrates the object 40 to be inspected, the ray beam further penetrates the third collimating list 30 and is received by the detector 32. The detector 32 sends the received data of ray beam to the imaging computer 5. The ray receiving unit 3 in the present embodiment further includes radiation guard component 33 which is configured for absorbing the ray beam 8 that penetrates the third collimator 31 but is not absorbed by the detector 32 for the purpose of radiation guard. In order to facilitate the control of the movement of the ray receiving unit 3, the third collimator 31, the detector 32 and the radiation guard component 33 in the present embodiment are bonded together.

The first collimator 1 and the third collimator 31 adopt heavy metal, such as lead. Therefore, the first collimator 1 and the third collimator 31 may be made comparatively thin so as to minimize the volume of the whole straight trajectory CT device and to reduce the space occupied.

Further, in the present embodiment, the first track 19 and the second track 39 are arranged on both sides of the channel 4 for the objects to be inspected. The first track 19, the channel 4 for the objects to be inspected and the second track 39 are parallel to one another (of course, in principle it will be sufficient that the first track 19 and the second track 39 are parallel to each other, they may not be parallel to the channel 4 for the objects to be inspected. Herein the preferably embodiment is provided). The first collimator 1 moves on the first track 19 and the third collimator 31 movers on the second track 39 (because all the components of the ray receiving unit 3 are bonded together, the ray receiving unit 3 moves on the second track 39).

The ratio of the width of the first collimating slit 10 to the width of the third collimating slit 30 may be equal to the ratio of the distance from the ray source 22 to the first track 19 to the distance from the ray source 22 to the second track 39 so as to make the third collimator 31 to perform collimation. As to the cone beam three dimensional scanning, the above-mentioned ratio of the distance from the ray source 22 to the first track 19 to the distance from the ray source 22 to the second track 39 may be altered to the ratio of the distance from the projection of the ray source 22 on the horizontal plane to the projection of the first track 19 on the horizontal plane to the distance from the projection of the ray source 22 on the horizontal plane to the projection of the second track 39 on the horizontal plane.

When scanning the object 40 to be inspected, the ray source 22 and the second collimator 21 are static while the first collimator 1 moves along the first track 19 and the ray receiving unit 3 (including the third collimator 31, detector 32 and radiation guard component 33) moves along the second track 39. The direction toward which the first collimator 1 moves is same as that the ray receiving unit 3 moves toward. In addition, during the movement, the ray source 22, the first collimating slit 10 and the third collimating slit 30 are kept aligned on one line. This could be achieved by controlling the ratio of the velocity of movement of the first collimator 1 to the third collimator 31. That is, the ratio of the velocity of movement of the first collimator 1 to the third collimator 31 is equal to the ratio of the distance from the ray source 22 to the first track 19 and the distance from the ray source 22 to the second track 39.

During scanning inspection, the object 40 to be inspected passes through the channel 4 for the object to be inspected slowly. For example, the velocity of the object 40 to be inspected may be 0.5 percent to 10 percent, e.g. thirtieth, fortieth, fiftieth or the like of the velocity of the ray receiving unit 3. The first collimator 1 and the third collimator 31 may reciprocate on their tracks (the first track 19, the second track 39) respectively so as to scan the object 40 to be inspected in each angle. The detector 32 may collect data during the reciprocation. Alternatively it may collect data in either one direction of the reciprocation. Herein, specific limitation will not be given.

Further, the straight trajectory CT device in the present embodiment may further include a data processing unit, a control unit and an alarm unit etc. The data processing unit comprises an imaging computer which processes the obtained data after receiving the data sent by the detector 32 so as to reconstruct the image and display it. Data processing unit is also used for user to interact and send control instructions to the alarming unit as necessary. The alarming unit is used for alarming upon receiving the control instruction generated by the data processing system. The control unit is used to control and monitor the moving condition of the first collimator 1 and the ray receiving unit 3 on their respective tracks. The control unit may used to control the ray source 22 to generate ray beam 8 or stop generating ray beam 8. The control unit may also used to control or monitor the movement of the object 40 to be inspected.

Embodiment 3

Figure 3:
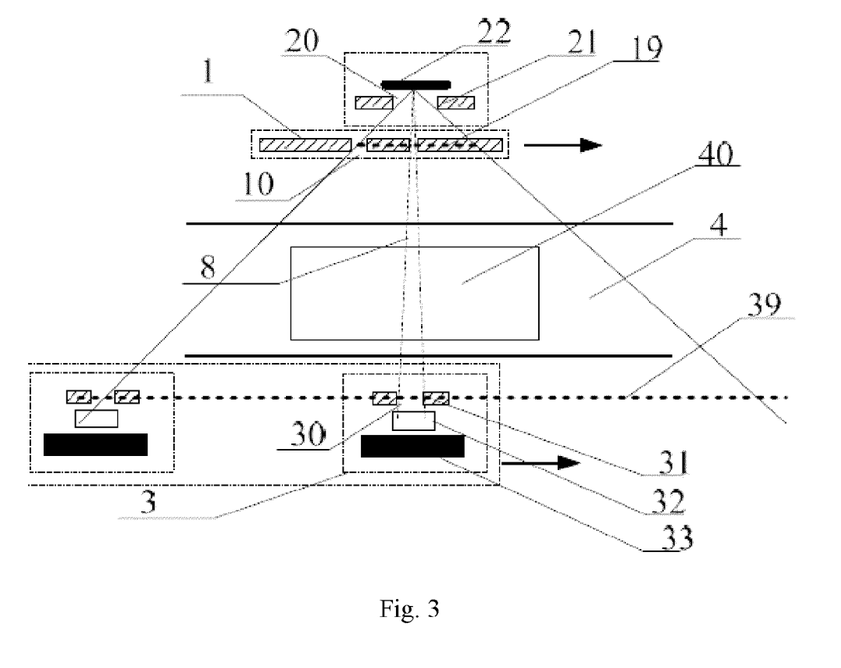
FIG. 3 is a schematic view of the structure of a straight trajectory CT device according to embodiment 3 of the present invention.

The straight trajectory CT device of the present application is shown in FIG. 3. The structure of the straight trajectory CT device is substantially same as that in the embodiment 1. The distinction mainly lies in that two of the first collimating slits 10 are provided on the first collimator 1 in the present embodiment. Correspondingly, the number of the ray receiving units 3 is two. Each of the ray receiving units 3 corresponds to a first collimating slit 10.

As to the straight trajectory CT device in the embodiment 1, if the maximum stroke of the unidirectional movement of the first collimating slit 10 is s, then the distance between the two centers of the first collimating slit 10 equals to s/2 in the present embodiment. The first collimator 1 in the present embodiment may be obtained by altering the first collimator 1 in the embodiment 1, for example, a new first collimating slit 10 may be added on the basis of the first collimator 1 in the embodiment 1 with the added slit located on the left side or the right side of the first collimator 1; meanwhile, it must make sure the boundary of the first collimator 1 is beyond the range of the field angle, that is to say, wherever the first collimator 1 moves, it should cover the whole specific range of the field angle defined by the ray generating unit 2 so as to absorb and obstruct the ray beam that does not penetrate the first collimating slit 10 for the purpose of radiation guard. Certainly, the first collimator 1 in the present embodiment may also be provided individually instead of being altered by the first collimator 1 in the embodiment 1.

When scanning the object 40 to be inspected, the ray source 22 and the second collimator 21 are static, while the first collimator 1 moves along the first track 19 and two ray receiving units 3 (both include the third collimator 31, detector 32 and radiation guard component 33) move along the second track 39. The direction toward which the first collimator 1 moves is the same as that the ray receiving unit 3 moves toward. In addition, during the movement, the ray source 22, any one of the first collimating slit 10 and the third collimating slit 30 corresponding to this first collimating slit 10 are kept aligned on one line. Namely, the ray source 22, the first collimating slit 10 on the left side, the third collimating slit 30 of the ray receiving unit 3 on the left side are kept aligned on one line, while the ray source 22, the first collimating slit 10 on the right side, the third collimating slit 30 of the ray receiving unit 3 on the right side are kept aligned on one line. This could be achieved by controlling the ratio of the velocity of movement of the first collimator 1 to the third collimator 31. That is, the ratio of the velocity of movement of the first collimator 1 to the third collimator 31 is equal to the ratio of the distance from the ray source 22 to the first track 19 and the distance from the ray source 22 to the second track 39.

During scanning inspection, the object 40 to be inspected passes through the channel 4 for the object to be inspected slowly. For example, the velocity of the object 40 to be inspected may be 0.5 percent to 10 percent, e.g. thirtieth, fortieth, fiftieth or the like of the velocity of the ray receiving unit 3. The first collimator 1 and the third collimator 31 may reciprocate on their tracks respectively so as to scan the object 40 to be inspected in each angle. The detector 32 may collect data during the reciprocation. Alternatively it may collect data in either one direction of the reciprocation. Herein, specific limitation will not be given.

Compared with the straight trajectory CT device in the embodiment 1, the device in the present embodiment may conduct a quicker scanning inspection with the scanning rate twice as that of the straight trajectory CT device provided in the embodiment 1. Meanwhile, compared with the straight trajectory CT device in the prior art, the number of ray receiving unit 3 is decreased and there is little crosstalk between the ray receiving units.

Embodiment 4

Figure 4:
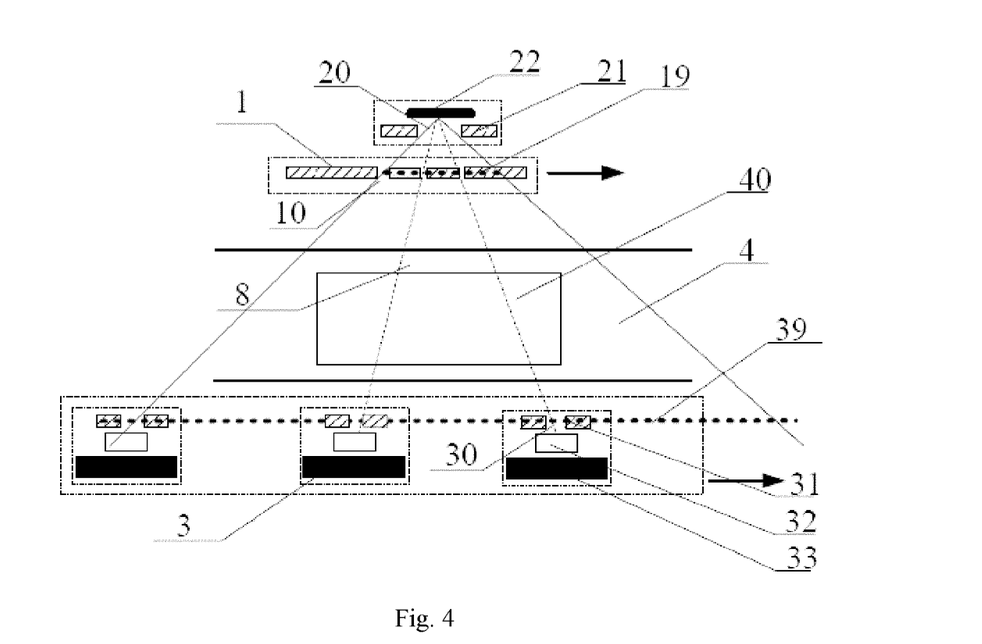
FIG. 4 is a schematic view of the structure of a straight trajectory CT device according to embodiment 4 of the present invention.

The straight trajectory CT device of the present application is shown in FIG. 4. The structure of the straight trajectory CT device is substantially same as that in the embodiment 1. The distinction mainly lies in that three of the first collimating slits 10 are provided on the first collimator 1 in the present embodiment. Correspondingly, the number of the ray receiving units 3 is three. Each of the ray receiving unit 3 corresponds to a first collimating slit 10.

As to the straight trajectory CT device in the embodiment 1, if the maximum stroke of the unidirectional movement of the first collimating slit is s, then the distance between the centers of the two adjacent first collimators 10 equals to s/3 in the present embodiment. The first collimator 1 in the present embodiment may be obtained by altering the first collimator 1 in the embodiment 1, for example, two new first collimating slits 10 may be added on the basis of collimator 1 in the embodiment 1; meanwhile, it must make sure the boundary of the first collimator 1 is beyond the range of the field angle, that is to say, wherever the first collimator 1 moves, it should cover the whole specific range of the field angle defined by the ray generating unit 2 so as to absorb and obstruct the ray beam 8 that does not penetrate the first collimating slit 10 for the purpose of radiation guard. Certainly, the first collimator 1 in the present embodiment may also be provided individually instead of being altered by the first collimator 1 in the embodiment 1.

When scanning the object 40 to be inspected, the ray source 22 and the second collimator 2 are static while the first collimator 1 moves along the first track 19 and three ray receiving units 3 (each including the third collimator 31, detector 32 and radiation guard component 33) move along the second track 39. The direction toward which the first collimator 1 moves is same as that the ray receiving unit moves toward. In addition, during the movement, the ray source 22, any one of the first collimating slits 10 and the third collimating slit 30 corresponding to this first collimating slit are kept aligned on one line. Namely, the ray source 22, the first collimating slit 10 on the left side, the third collimating slit of the ray receiving unit 3 on the left side are kept aligned on one line; the ray source 22, the medial first collimating slit 10, the medial third collimating slit 30 of the ray receiving unit 3 are kept aligned on one line, while the ray source 22, the first collimating slit 10 on the right side, the third collimating slit 30 of the ray receiving unit 3 on the right side are kept aligned on one line. This could be achieved by controlling the ratio of the velocity of movement of the first collimator 1 to the third collimator 30. That is, the ratio of the velocity of movement of the first collimator 1 to the third collimator 31 is equal to the ratio of the distance from the ray source 22 to the first track 19 and the distance from the ray source 22 to the second track 39.

During scanning inspection, the object 40 to be inspected passes through the channel 4 for the object to be inspected slowly. For example, the velocity of the object 40 to be inspected may be 0.5 percent to 10 percent, e.g. thirtieth, fortieth, fiftieth or the like of the velocity of the ray receiving unit 3. The first collimator 1 and the third collimator 31 may reciprocate on their tracks respectively so as to scan the object 40 to be inspected in each angle. The detector 32 may collect data during the reciprocation. Alternatively it may collect data in either one direction of the reciprocation. Herein, specific limitation will not be given.

Compared with the straight trajectory CT device in the embodiment 1, the device in the present embodiment may conduct a quicker scanning inspection with the scanning rate three times as that of the straight trajectory CT device provided in the embodiment 1. Meanwhile, compared with the straight trajectory CT device in the prior art, the number of ray receiving unit 3 is decreased and there is little crosstalk between the ray receiving units 3.

Obviously, in the straight trajectory CT device in the present application, the number of the first collimating slit 10 provided on the first collimator 1 may be other numerical value. For example, n (n is the integral number greater than 3) of the first collimating slits 10 may be provided on the first collimator 1 through which the ray beam could pass. The first collimating slit 10 is within the range of the field angle and the boundary of the first collimator 1 is beyond the range of the field angle. The number of the ray receiving units 3 is equal to the number of the first collimating slits 10. Each ray receiving unit 3 corresponds to one of the first collimating slit 10. As to the straight trajectory CT device in the embodiment 1, if the maximum stroke of the unidirectional movement of the first collimating slit 10 is s, then the distance between the centers of adjacent first collimating slit 10 equals to s/n where n of the first collimating slits 10 are provided on the first collimator 1. The scanning rate of the device in the present embodiment is n times as that of the straight trajectory CT device provided in the embodiment 1. Herein unnecessary details will not be given.

Embodiment 5

The present embodiment provides a straight trajectory X-ray imaging device, which is similar to the straight trajectory tomography scanning device in the embodiments 1-4. However, when scanning the object to be inspected, the inspected object keeps static instead of moving. What's more, the first collimator 1 and the ray receiving unit 3 do not reciprocate, but perform a unidirectional movement for only once. A detector 32 only collects data during that unidirectional movement. Thus the straight trajectory CT device turns into a fluoroscopic scanning device on the basis of X-ray. Such device could realize quick scanning avoiding the image error caused by the movement of the object inspected.

Embodiment 6

Figure 5:
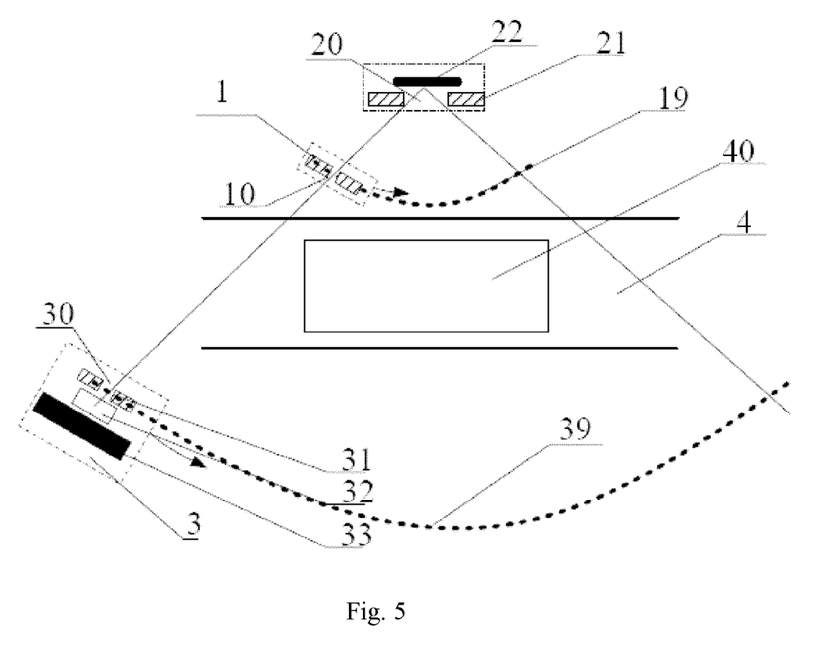
FIG. 5 is a schematic view of the structure of a straight trajectory CT device according to embodiment 6 of the present invention.

Similar to the straight trajectory tomography scanning device in the embodiments 1, 2, 3, or 4, referring to FIG. 5, the straight trajectory tracks (the first track 19, the second 39) on both sides of the channel for the object to be inspected in the present embodiment are replaced by arc tracks, the centers of their circle are located at the position of ray source. The first collimator 1 and the ray receiving unit 3 move on two arc tracks (the first track 19, the second track 39) respectively.

Compared with the device in the embodiments 1-3, this CT device occupies more space, but the consistency of the angles of the first collimating slit 10, the third collimating slit 30 and the ray source is higher and the consistency of the interval of the sampled data angles is readily to be achieved.

Figure 6:
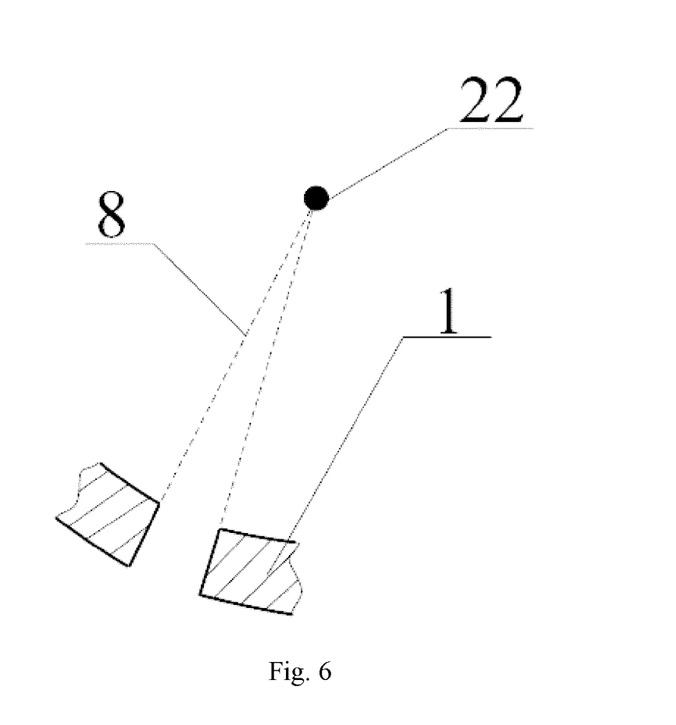
FIG. 6 is a schematic view of the structure of a first collimator and a third collimator according to embodiment 5 of the present invention.

Preferably, the first collimator 1 and the third collimator 31 are designed as shown in FIG. 6. The boundary of the first collimating slit 10 is in the direction of the radius of circle with the center thereof being the ray source 22. During the scanning inspection, the ray source 22, the first collimating slit 10, and the third collimating slit 30 are kept aligned on one line.

Preferably, the ratio of the width of the first collimating slit 10 to the third collimating slit 30 is the ratio of radiuses of the first track 19, the second track 39 (corresponding to the ratio of the distance from the ray source 22 to the first track 19 to the distance from the ray source 22 to the second track 39 in the embodiments 1-4).

Preferably, the ratio of the velocity of movement of the first collimator 1 on the first track 19 to the velocity of movement of the ray receiving unit 3 on the second track 39 is the ratio of the radiuses of their first tracks and second tracks.

Figure 7:
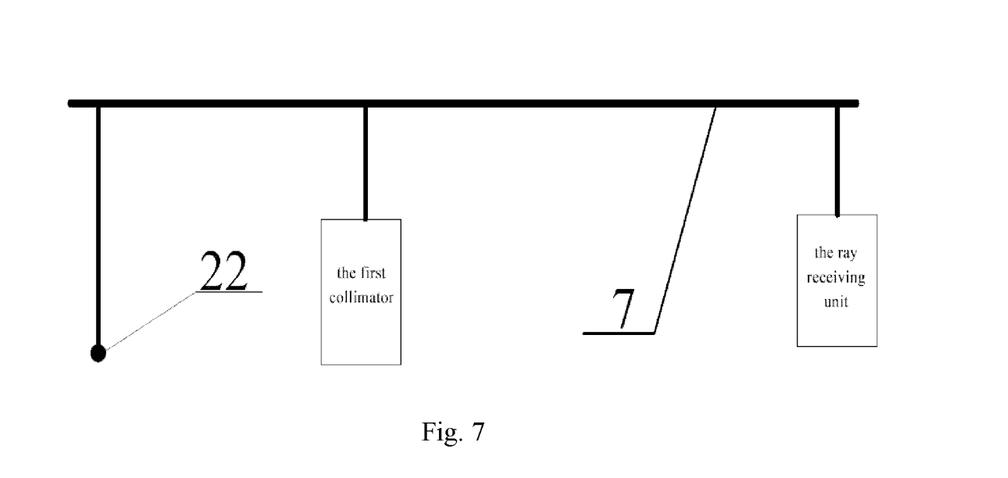
FIG. 7 is a schematic view of the structure of a ray source, a first collimator and a ray receiving unit according to embodiment 5 of the present invention.

As shown in FIG. 7, preferably, the ray source 22, the first collimator 1 and the ray receiving unit 3 are bridged together by the straight bar 7. Thus, As long as the movement of the ray receiving unit is only controlled, the first collimator 1 may follow to move automatically and keep the ray source 22, the first collimating slit 10 of the first collimator 1 and the third collimating slit 30 of the third collimator 31 aligned on one line. It is not difficult for those skilled in this art to apply the design of bridging the ray source 22, the first collimator 1 and the ray receiving unit 3 together by the straight bar 7 to the embodiments 1-4 following the inspiration of FIG. 7 to keep the ray source 22, the collimating slit 10 of the first collimator 1 and the third collimating slit 30 of the third collimator 31 aligned on one line. Certainly, there is a distinction that the first collimator 1 and the ray receiving unit 3 are moveable along the length of the straight bar 7 so as to meet the situation of straight trajectory of the embodiments 1-4.

As to other portions of the tomography detection device, the embodiments can be expanded according to embodiments 1-4. Herein unnecessary details will not be given.

As to the straight trajectory CT device, the ray source 22 is static, and the object 40 to be inspected moves in the channel 4 for the object to be inspected (the velocity thereof may be thirtieth, fortieth, fiftieth or the like of the velocity of the ray receiving unit 3). The first collimator 1 and ray receiving unit 3 may reciprocate on the arc track (the first track 19 and the second track 39). The detector 32 may collect data during the reciprocation. Alternatively it may collect data in either one direction of the reciprocation. Herein, specific limitation will not be given.

As to the imaging device, the ray source 22 is static and the object 40 inspected is static. The first collimator 1 and the ray receiving unit 3 perform a unidirectional movement for only once. Detector 32 only collects data during that unidirectional movement.

In conclusion, according to the CT device based on straight trajectory provided by the present application, by the first collimator provided between the ray receiving unit and the channel for the object to be inspected, the ray beam is received by the ray receiving unit after penetrating the first collimator and the object to be inspected in order. During scanning, the ray generating unit is static and the first collimator moves toward the same direction as the ray receiving unit moves toward and the moving direction is parallel to the channel for the object to be inspected. The scanning of the object to be inspected for each angle is achieved by the collaborating movement between the first collimator and the ray receiving unit. Therefore, the straight trajectory CT device of the present application can complete tomography scanning with the least one ray receiving unit, thereby simplifying the structure of the straight trajectory CT device and reducing its cost.

INDUSTRIAL APPLICATION

According to the CT device based on straight trajectory provided by the present application, by the first collimator provided between the ray receiving unit and the channel for the object to be inspected, the ray beam is received by the ray receiving unit after penetrating the first collimator and the object to be inspected in order. During scanning, the ray generating unit is static and the first collimator moves toward the same direction as the ray receiving unit moves toward and the moving direction is parallel to the channel for the object to be inspected. The scanning of the object to be inspected for each angle is achieved by the collaborating movement between the first collimator and the ray receiving unit. Therefore, the straight trajectory CT device of the present application can complete tomography scanning with the least one ray receiving unit, thereby simplifying the structure of the straight trajectory CT device and reducing its cost.

What is claimed is:

1. A CT device based on straight trajectory comprising:
a ray generator configured to generate a ray beam within a specific range of field angle;
a first collimator configured to restrain the ray beam;
a channel having a longitudinal axis, and configured to accept an object to be inspected to pass through; and
a ray receiver configured to receive the ray beam restrained by the first collimator;
wherein:
the ray receiver is configured to transmit data from a received ray beam to an imaging computer to process and display the data,
the ray generator is stationary, and the first collimator and the ray receiver are movable,
a first track and a second track parallel to each other provided on both sides of the channel, wherein the first track and the second track are straight tracks parallel to the channel, and
the first collimator and the ray receiver are configured to move in a same direction parallel to the longitudinal axis of the channel along the first track and second track, respectively, such that the ray beam generated by the ray generator is received by the ray receiver after penetrating the first collimator and the object to be inspected at any position within the channel in order.

2. The CT device according to claim 1, wherein:
the first collimator comprises at least one first collimating slit through which the ray beam passes,
the at least one first collimating slit is located within the specific range of field angle, and
the first collimator covers the specific range of field angle in its entirety, regardless of position thereof.

3. The CT device according to claim 2, wherein a distance between centers of adjacent first collimating slits of the at least one first collimating slit equals to s/n, where n is the number of the first collimating slits and greater than 1, and s is the maximum stroke of the unidirectional movement of the at least one first collimating slit when n equals to 1.

4. The CT device according to claim 2, wherein the number of the ray receivers is equal to the number of the at least one first collimating slit, and each ray receiver corresponds to respective at least one first collimating slit.

5. The CT device according to claim 4, wherein the ray receiver comprises a third collimator comprising a third collimating silt and a detector receiving the ray beam that penetrates the third collimator.

6. The CT device according to claim 1, wherein the ray generator comprises a ray source generating the ray beam and a second collimator which defines the ray beam in the specific range of field angle.

7. The CT device according to claim 1, wherein the ray generator, the first collimator and the ray receiver are fixed on a straight bar.

8. The CT device according to claim 1, wherein the ray receiver further comprises a radiation guard component for absorbing the ray beam that is not absorbed by the ray receiver.

9. The CT device according to claim 1, wherein when in use, the first collimator and the ray receiver are configured to perform reciprocation while the object to be inspected moves in the channel.

10. The CT device according to claim 9 further comprising a controller capable of controlling and monitoring a moving condition of the first collimator and the ray receiver.

11. The CT device according to claim 10, wherein the controller is configured to set a velocity of the object to be inspected is 0.5 percent to 10 percent of the velocity of the ray receiver.

12. A straight trajectory X-ray imaging device comprising:
a ray generator configured to generate a ray beam within a specific range of field angle,
a first collimator configured to restrain the ray beam;
a channel having a longitudinal axis, and configured to accept an object to be inspected to pass through; and
a ray receiver configured to receive the ray beam restrained by the first collimator;
wherein
the ray receiver is configured to transmit data from a received ray beam to an imaging computer to process and display the data;
the ray generator is stationary, and the first collimator and the ray receiver are movable,
a first track and a second track parallel to each other provided on both sides of the channel, wherein the first track and the second track are straight tracks parallel to the channel, and
the first collimator and the ray receiver are configured to move in a same direction parallel to the longitudinal axis of the channel along the first track and second track, respectively, such that the ray beam generated by the ray generator is received by the ray receiver after penetrating the first collimator and the object to be inspected at any position within the channel in order, when in use, the first collimator and the ray receiver are configured to perform a unidirectional movement only once, while the object to be inspected is stationary in the channel.

* * * * *